(12) United States Patent
Jones

(10) Patent No.: US 9,005,171 B2
(45) Date of Patent: Apr. 14, 2015

(54) RESETTABLE DRUG DELIVERY DEVICE

(75) Inventor: Christopher Jones, Tewkesbury (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 7 days.

(21) Appl. No.: 13/375,182

(22) PCT Filed: May 28, 2010

(86) PCT No.: PCT/EP2010/057471
§ 371 (c)(1),
(2), (4) Date: Mar. 9, 2012

(87) PCT Pub. No.: WO2010/139632
PCT Pub. Date: Dec. 9, 2010

(65) Prior Publication Data
US 2012/0165744 A1 Jun. 28, 2012

Related U.S. Application Data

(60) Provisional application No. 61/182,831, filed on Jun. 1, 2009.

(30) Foreign Application Priority Data

Jul. 10, 2009 (EP) .................................. 09009053

(51) Int. Cl.
  *A61M 5/00* (2006.01)
  *A61M 5/24* (2006.01)
  *A61M 5/315* (2006.01)

(52) U.S. Cl.
  CPC .............. *A61M 5/24* (2013.01); *A61M 5/31535* (2013.01); *A61M 5/31551* (2013.01); *A61M 5/31585* (2013.01); *A61M 2005/2488* (2013.01); *A61M 5/31543* (2013.01)

(58) Field of Classification Search
  CPC .............. A61M 5/24; A61M 5/31535; A61M 5/31551; A61M 5/31585; A61M 5/31543; A61M 2005/2488
  USPC .................................. 604/187, 189, 207–211
  See application file for complete search history.

(56) References Cited

U.S. PATENT DOCUMENTS 3,302,462 A   2/1967   Pursell
5,514,097 A   5/1996   Knauer
(Continued)

FOREIGN PATENT DOCUMENTS

DE   93 01 334 U1    4/1993
DE   197 30 999 C1  12/1998
(Continued)

OTHER PUBLICATIONS

European Search Report for EP Application No. 09009053, completed Aug. 31, 2010.
(Continued)

*Primary Examiner* — Theodore Stigell
(74) *Attorney, Agent, or Firm* — McDonnell Boehnen Hulbert & Berghoff LLP

(57) ABSTRACT

A resettable dosing mechanism comprises a dose button and a dial grip operatively coupled to the dose button. A spindle acts on a bung of a cartridge and a driver is operatively coupled between the dose button and the spindle. During an injection of the dose, the dose button moves in an axial direction to cause the spindle to administer the dose. During resetting of the dose setting mechanism, the spindle is retracted back into the dose setting mechanism. An advantageous resetting mechanism is described.

12 Claims, 7 Drawing Sheets

(56) References Cited

U.S. PATENT DOCUMENTS

| | | | |
|---|---|---|---|
| 5,584,815 A | 12/1996 | Pawelka et al. | |
| 5,591,136 A | 1/1997 | Gabriel | |
| 5,792,117 A | 8/1998 | Brown | |
| 5,820,602 A | 10/1998 | Kovelman et al. | |
| 6,090,080 A * | 7/2000 | Jost et al. | 604/207 |
| 6,936,032 B1 | 8/2005 | Bush, Jr. et al. | |
| 7,195,616 B2 | 3/2007 | Diller et al. | |
| 2004/0127858 A1 | 7/2004 | Bendek et al. | |
| 2004/0162528 A1 | 8/2004 | Horvath et al. | |
| 2004/0186437 A1 | 9/2004 | Frenette et al. | |
| 2004/0210199 A1 | 10/2004 | Atterbury et al. | |
| 2004/0236285 A1 | 11/2004 | Fisher et al. | |
| 2004/0267207 A1* | 12/2004 | Veasey et al. | 604/208 |
| 2005/0137571 A1 | 6/2005 | Hommann | |
| 2006/0153693 A1 | 7/2006 | Fiechter | |
| 2006/0258988 A1 | 11/2006 | Keitel et al. | |
| 2007/0021718 A1 | 1/2007 | Burren et al. | |
| 2007/0111175 A1 | 5/2007 | Raven et al. | |
| 2007/0276341 A1 | 11/2007 | Graf et al. | |
| 2008/0027397 A1 | 1/2008 | DeRuntz et al. | |
| 2008/0077095 A1 | 3/2008 | Kirchhofer | |
| 2008/0208123 A1 | 8/2008 | Hommann | |
| 2009/0227959 A1 | 9/2009 | Hirschel et al. | |

FOREIGN PATENT DOCUMENTS

| | | |
|---|---|---|
| DE | 298 18 721 U1 | 3/2000 |
| DE | 10 2005 063 311 | 8/2006 |
| DE | 10 2005 060 928 | 6/2007 |
| DE | 10 2006 038 123 | 2/2008 |
| DE | 10 2007 026 083 | 11/2008 |
| EP | 1 944 050 | 9/1986 |
| EP | 0 897 728 | 2/1999 |
| EP | 0 937 471 | 8/1999 |
| EP | 0 937 472 | 8/1999 |
| EP | 1 541 185 | 6/2005 |
| EP | 1 776 975 | 4/2007 |
| EP | 1 923 084 | 5/2008 |
| GB | 2 443 390 | 5/2008 |
| JP | 2005-531348 | 10/2005 |
| JP | 2006-519075 | 8/2006 |
| JP | 2008-517233 | 5/2008 |
| WO | 92/18180 | 10/1992 |
| WO | 93/07922 | 4/1993 |
| WO | 96/23973 | 8/1996 |
| WO | 96/39214 | 12/1996 |
| WO | 97/10864 | 3/1997 |
| WO | 98/01171 | 1/1998 |
| WO | 99/03520 | 1/1999 |
| WO | 01/10484 | 2/2001 |
| WO | 01/19434 | 3/2001 |
| WO | 02/051471 | 7/2002 |
| WO | 02/092153 | 11/2002 |
| WO | 03/080160 | 10/2003 |
| WO | 2004/002556 | 1/2004 |
| WO | 2004/020028 | 3/2004 |
| WO | 2004/030730 | 4/2004 |
| WO | 2004/047893 | 6/2004 |
| WO | 2004/064900 | 8/2004 |
| WO | 2004/064902 | 8/2004 |
| WO | 2004/078240 | 9/2004 |
| WO | 2004/078241 | 9/2004 |
| WO | 2004/078242 | 9/2004 |
| WO | 2004/078293 | 9/2004 |
| WO | 2005/018721 | 3/2005 |
| WO | 2005/021072 | 3/2005 |
| WO | 2005/039676 | 5/2005 |
| WO | 2005/044346 | 5/2005 |
| WO | 2005/123159 | 12/2005 |
| WO | 2006/024461 | 3/2006 |
| WO | 2006/045528 | 5/2006 |
| WO | 2006/058883 | 6/2006 |
| WO | 2006/079481 | 8/2006 |
| WO | 2006/089767 | 8/2006 |
| WO | 2006/114395 | 11/2006 |
| WO | 2006/125328 | 11/2006 |
| WO | 2007/017052 | 2/2007 |
| WO | 2007/067889 | 6/2007 |
| WO | 2008/031235 | 3/2008 |
| WO | 2008/074897 | 6/2008 |
| WO | 2008/116766 | 10/2008 |
| WO | 2008/128373 | 10/2008 |

OTHER PUBLICATIONS

Partial European Search Report for EP Application No. 09009053, completed Jun. 23, 2010.
International Search Report and Written Opinion for International App. No. PCT/EP2010/057471, completed Dec. 22, 2010.
Invitation to Pay Additional Fees, form PCT/ISA/206, for International App. No. PCT/EP2010/057471, completed Dec. 22, 2010.
International Preliminary Report on Patentability, for International App. No. PCT/EP2010/057471, completed Sep. 8, 2011.
Office Action issued for Russian Patent App. No. 2011154022/14(081248), issued Apr. 25 2014.
Office Action for Japanese Patent App. No. 2012-513562, mailed Apr. 1, 2014.

* cited by examiner

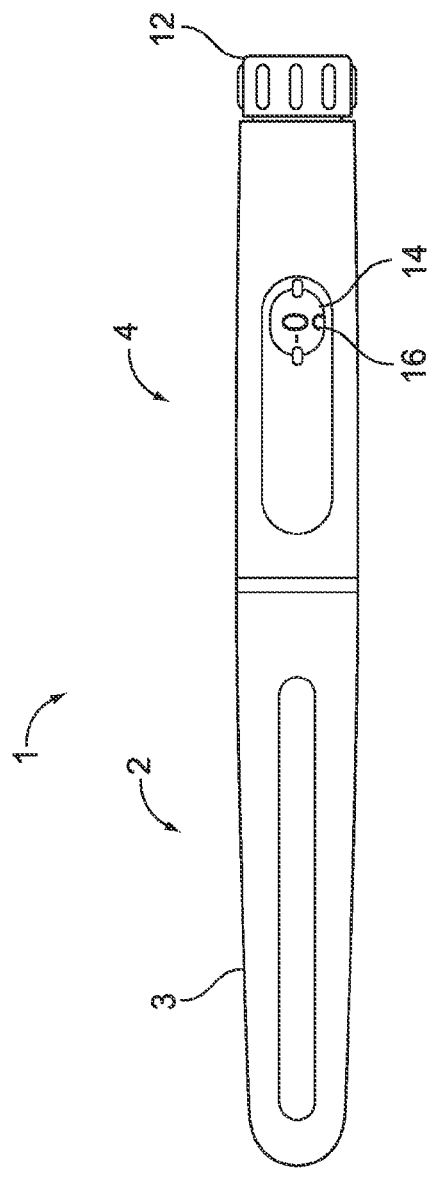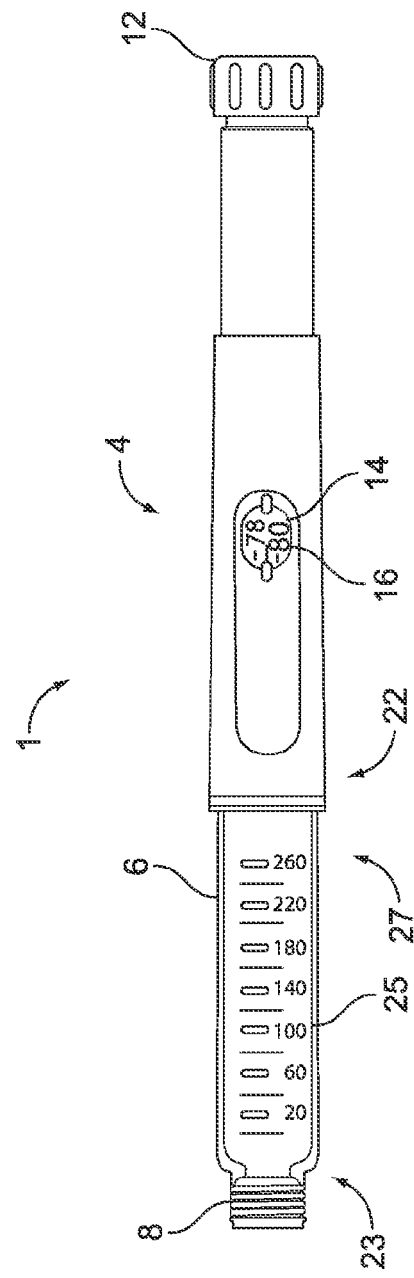

RESETTABLE DRUG DELIVERY DEVICE

CROSS REFERENCE TO RELATED APPLICATIONS

The present application is a U.S. National Phase Application pursuant to 35 U.S.C. §371 of International Application No. PCT/EP2010/057471 filed May 28, 2010, which claims priority to U.S. Provisional Patent Application No. 61/182,831 filed on Jun. 1, 2009 and to European Patent Application No. 09009053.1 filed on Jul. 10, 2009. The entire disclosure contents of these applications are herewith incorporated by reference into the present application.

FIELD OF INVENTION

The present application is generally directed to dose setting mechanisms for drug delivery devices. More particularly, the present application is generally directed to resettable dose setting mechanisms for drug delivery devices.

Pen type drug delivery devices provide for self administration of medicinal product from a multi-dose cartridge. A resettable pen type drug delivery device allows a user to replace an empty multi-dose cartridge with a new cartridge. Consequently, the user is called upon to re-set a dose setting mechanism of the drug delivery device. Aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease.

Pen type drug delivery devices have application where regular injection by persons without formal medical training occurs. This may be increasingly common among patients having diabetes where self-treatment enables such patients to conduct effective management of their disease.

There are basically two types of pen type delivery devices: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then a dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

Different types of pen delivery devices, including disposable (i.e., non-resettable) and reusable (i.e., resettable) varieties, have evolved over the years. For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

In contrast to typical disposable pen type devices, typical reusable pen delivery devices feature essentially two main reusable components: a cartridge holder and a dose setting mechanism. After a cartridge is inserted into the cartridge holder, this cartridge holder is attached to the dose setting mechanism. The user uses the dose setting mechanism to select a dose. Before the user injects the set dose, a replaceable double-ended needle assembly is attached to the cartridge housing.

This needle assembly may be threaded onto or pushed onto (i.e., snapped onto) a distal end of the cartridge housing. In this manner, a double ended needle is mounted on the needle assembly penetrated through a pierceable seal at a distal end of the cartridge. After an injection, the needle assembly is removed and discarded. After the insulin in the cartridge has been exhausted, the user detaches the cartridge housing from the dose setting mechanism. The user can then remove the empty cartridge from the cartridge retainer and replace the empty cartridge with a new (filled) cartridge.

Aside from replacing the empty cartridge with a new cartridge, the user must somehow prepare the dose setting mechanism for a new cartridge: the dose setting mechanism must be reset to a starting or initial position. For example, in certain typical resettable devices, in order to reset the dose setting mechanism, the spindle that advances in a distal direction during dose injection must somehow be retracted back into the dose setting mechanism. Certain known methods of retracting this spindle back into the dose setting mechanism to a restart or an initial position are known in the art. As just one example, known reset mechanisms require a user to turn back or push back (retract) the spindle or some other portion of the dose setting mechanism. Additionally, a so called last dose mechanism which represents the amount of medication contained in the cartridge must be reset.

Resetting of known dose setting mechanisms have certain perceived disadvantages. One perceived disadvantage is that the pen device user has to disassemble the device to either remove an empty cartridge or somehow reset the device. As such, another perceived disadvantage is that such devices have a high number of parts and therefore such devices are typically complicated from a manufacturing, from an assembly and an handling standpoint. For example, certain typical resettable pen type devices are not intuitive as to how a user must replace an empty cartridge and reset the device. In addition, because such resettable devices use a large number of components parts, such resettable devices tend to be large and bulky, and therefore not easy to carry around or easy to conceal.

It is therefore the object of the present invention to improve the drug delivery device as well as the dosing mechanism with regard to these disadvantages associated with resetting issues. Such desired drug delivery devices would tend to reduce the number of component parts and also tend to reduce manufacturing costs while also making the device less complex to assemble and manufacture. Such desired devices would also tend to simplify the steps required for a user to reset a dose setting mechanism while also making the device less complex and more compact in size.

SUMMARY

According to an exemplary embodiment of the present invention solving above object, a resettable dosing mechanism comprises a dose button and a dial grip operatively coupled to the dose button. A spindle acts on a bung of a cartridge and a driver is operatively coupled between the dose button and the spindle. During an injection of the dose, said dose button moves in an axial direction to cause said spindle to administer said dose. The dosing mechanism further comprises a resetting mechanism, wherein during resetting of the dose setting mechanism using said resetting mechanism, the spindle is preferably retracted back into the dose setting mechanism.

In another exemplary embodiment, a resettable dose setting mechanism comprises a preferably inner housing preferably having a helical groove. A dose dial sleeve is rotationally engaged with the housing, preferably with the helical groove of the housing. A driver is provided within the inner housing. The dose setting mechanism takes at least three different conditions using a first clutch provided between the dial sleeve and the driver and a second clutch provided between said housing and said driver. When a dose is set, the first clutch engages and the dial sleeve and the driver rotate together relative to the housing. When the dose is injected, the first clutch disengages the dose dial sleeve from the driver while the second clutch couples the driver to the inner housing, so that the dose dial sleeve rotates and the driver is prevented from rotating but moves axially against a spindle to expel the set dose. When resetting the dose setting mechanism, the first clutch decouples the driver from the dial sleeve and said second clutch decouples said driver from said housing, allowing the driver to be moved to a reset position.

In yet another arrangement, a resettable drug delivery device comprises a cartridge holder comprising a releasable mechanical interlock. A preferably above described resettable dose setting mechanism (dosing mechanism) is releasably coupled to the interlock. The dose setting mechanism comprises a dose button, a transfer sleeve, and a rotatable dose setting sleeve. When the dose setting sleeve is rotated to reach a predetermined position, the dose setting sleeve releases the mechanical interlock and places the resettable dose setting mechanism in a reset condition.

The above inventive solution requires a low part count and low complexity at the heart of the drug delivery device where space is limited. Further, the inventive solution does not expose plastic features to prolonged periods of load and has stiff and direct load paths.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates a first embodiment of a resettable drug delivery device;

FIG. 2 illustrates the resettable drug delivery device of FIG. 1 with the cap removed and with a dose having been dialled;

DETAILED DESCRIPTION

Figure 3:
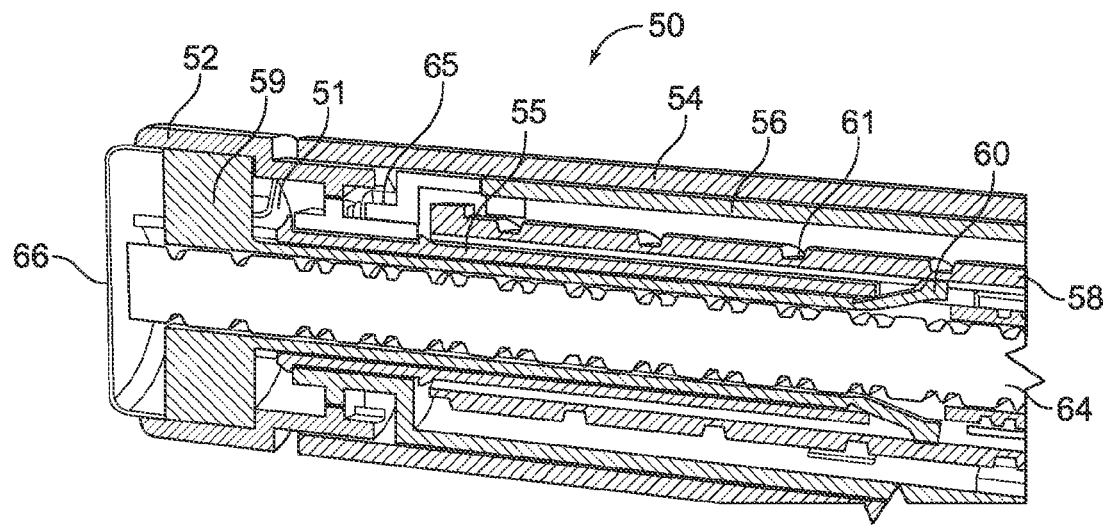
FIG. 3 illustrates a sectional view of a first arrangement of a dose setting mechanism, such as the dose setting mechanism of the drug delivery device illustrated in FIG. 1 in a dose dialling state.

The terms "drug" or "medicinal product" or "medicament", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device is a resettable drug delivery device (i.e., a reusable device). A first end of the cartridge retaining part 2 and a second end 22 of the dose setting mechanism 4 are secured together by connecting features. For this resettable device, these connecting features are releasable connecting features such as a thread, bayonet coupling or other similar connecting features.

In this illustrated arrangement, the cartridge housing 2 is secured within the second end 22 of the dose setting mechanism 4. A removable cap 3 is releasably retained over a second end or distal end 23 of a cartridge retaining part or cartridge housing 6. The dose setting mechanism 4 comprises a dose dial grip 12 and a window or lens 14. A dose scale arrangement 16 is viewable through the window or lens 14. To set a dose of medication contained within the drug delivery device 1, a user rotates the dose dial grip 12 such that a dialled dose will become viewable in the window or lens 14 by way of the dose scale arrangement 16.

FIG. 2 illustrates the medical delivery device 1 of FIG. 1 with the cap (cover) 3 removed from a distal end of the medical delivery device 1. This removal exposes the cartridge housing 6. As illustrated, a cartridge 25 from which a number of doses of a medicinal product may be dispensed, is provided in the cartridge housing 6. Preferably, the cartridge 25 contains a type of medicament that can be administered relatively often, such as once or more times a day. One such medicament is either long acting or short acting insulin or an insulin analog. The cartridge 25 comprises a bung or stopper (not illustrated in FIG. 2) that is retained near a second end or a proximal end of the cartridge 25. The medical delivery device also comprises a driver having a spindle (not illustrated in FIG. 2).

The cartridge housing 6 has a distal end 23 and a proximal end 27. Preferably, the cartridge distal end 23 of the cartridge housing 6 comprises a groove 8 for attaching a removable needle assembly. However, other needle assembly connection mechanisms could also be used. The cartridge proximal end 27 is removably connected to the dose setting mechanism 4. In one preferred embodiment, cartridge housing 6 proximal end 27 is removably connected to the dose setting mechanism 4 distal end 22 via a bayonet connection. However, as those of ordinary skill in the art will recognize, other types of removable connection methods such as threads, partial threads, ramps and detents, snap locks, snap fits, and luer locks may also be used.

The cartridge 25 is removable from the cartridge housing 6. The cartridge 25 may be removed from the device 1 without destroying the device 1 by merely having the user disconnect the dose setting mechanism 4 from the cartridge housing 6.

In use, once the cap 3 is removed, a user can attach a suitable needle assembly to the groove 8 provided at the distal end 23 of the cartridge housing 6. Such needle assembly may be, for example, screwed onto the distal end 23 of the housing 6 or alternatively may be snapped onto this distal end 23. After use, the replaceable cap 3 may be used to re-cover the cartridge housing 6. Preferably, the outer dimensions of the replaceable cap 3 are similar or identical to the outer dimensions of the dose setting mechanism 4 so as to provide an impression of a unitary whole when the replaceable cap 3 is in position covering the cartridge housing 6 when the device is not in use.

Figure 4:
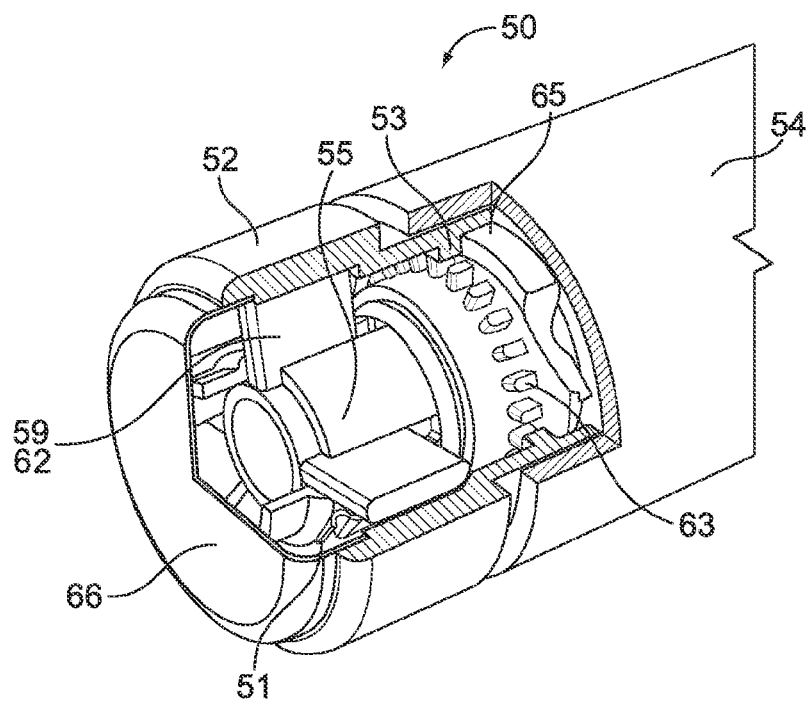
FIG. 4 is a partial perspective view of the dose setting mechanism illustrated in FIG. 3.

FIG. 3 illustrates a cross sectional view of a first arrangement of a dose setting mechanism 50, such as the dose setting mechanism 4 illustrated in FIG. 2 in a condition where the user is dialling a dose to be dispensed. Those of skill in the art will recognize that dose setting mechanism 50 may include a connection mechanism for releasably connecting to a cartridge holder, like the cartridge holder 6 illustrated in FIG. 2. FIG. 4 is a partial perspective view of the dose setting mechanism illustrated in FIG. 3.

With reference to FIGS. 3 and 4, the dose setting mechanism 50 comprises a button 66, a dose dial grip 52, a spring 51, an outer housing 54, a clutch sleeve 59 with four wing features 62 accommodated at its proximal end, a driver 55, a dial sleeve 56, an inner housing 58, and a spindle 64. As clearly seen from FIG. 4, the driver 55 is coupled to the clutch sleeve 59 by means of finger elements (clicker) 60 each protruding outwardly from the clutch sleeve 59 and into a respective opening or slot of the driver 55 each forming a close rotational fitting between the finger element 60 and the respective slot. The finger elements 60 slide over longitudinal grooves on the inner surface of the inner housing 58 and are free to move (bend) inwardly in radial direction and are not rigidly locked thus producing a clicker sound when rotating relative to the inner housing 58.

The clicker arrangement comprising finger 60 and a dispense clicker 65 of the dial sleeve 56 (described below) has the advantage, that finger 60 gives strong feedback during dialling, dispense clicker 65 gives light feedback during dispense in order to minimize losses, shows no overlapping or simultaneous clicks and disengages clickers during reset in order to minimize losses as well. Additionally, the close rotational fitting between fingers of the clutch sleeve create a rigid torsional load path from inner housing 58 to the spindle 64.

Further, the clutch sleeve 59 is coupled to the driver 55 by the wing features 62 which are movable in axial direction accommodated within longitudinal openings of the driver 55. The wing features 62 are further used for connection to the dial grip 52. The wing features 62 provide a rigid axial and rotational coupling with the dial grip 52 and the driver 55.

As illustrated, the outer housing 54 surrounds the various components making up the dose setting mechanism 50. The inner housing 58 has an outer surface comprising a helical groove 61. The dial sleeve 56 comprises a male groove member that engages the helical groove 61. Because of this rotational engagement, during a dose setting step, the dial sleeve 56 translates along this groove 61 in a proximal direction. In addition, the driver 55 is threadedly engaged with a portion of the spindle 64 such that when the driver 55 is urged in a distal direction, the spindle 64 is likewise urged in a distal direction.

In addition, the dial sleeve 56 further comprises a set of circumferential teeth 63 that radiate out away from the dial sleeve 56. These circumferential teeth 63 are releasably coupled to a portion of the dose dial grip 52. In one preferred arrangement, the circumferential teeth 63 of the dial sleeve 56 releasably engage inner directed corresponding teeth 53 along a distal portion of the dose dial grip 52. Preferably, the teeth are arranged in the way that teeth 53 are accommodated in the grooves between the teeth 63 and vice versa. The engagement of the two sets of teeth 53, 63 can be clearly seen from FIG. 4. Consequently, in the position illustrated in FIG. 4, rotation of the dose dial grip 52 will in turn rotate both the driver 55 and the clutch sleeve 59. Since the clutch sleeve 59 is engaged with both the driver 55 and the dial sleeve 56, rotation of the dose dial grip 52 will result in relative rotation of the dial sleeve 56 as well outwards into direction D2 (i.e. in proximal direction). Rotation of the dial sleeve 56 causes a dose to be set, similar to the dose set with the drug delivery device 1 illustrated in FIG. 1.

Returning to FIG. 5, the spindle 64 is threadedly engaged with a portion of the inner housing 58. In this manner, an axial dispensing force on the spindle 64 in the distal direction D1 causes the spindle 64 to rotate due to this threaded connection. This rotation and axial movement of the spindle 64 is caused by an axial force applied by the driver 55 on to the spindle 64 via a threaded engagement as the driver 55 moves axially towards the distal end of the dose setting mechanism 50 caused by pressing the button 66.

The clutch sleeve 59 is prevented from disengaging the driver 55 since the clutch sleeve 59 is splined to the driver 55 by the finger element 60 preventing relative rotation between these two components. During dispense the clicker 60 is additionally locked in splined engagement to the inner housing 58 because the outer surface of driver 55 prevents the distal end of the clicker 60 from moving and bending inwardly. Further, the inner housing 58 comprises longitudinal grooves receiving the distal ends of the finger elements 60. Therefore, the driver 55 cannot rotate relative to either the inner housing 58, the clutch sleeve 59 or the dial grip 52. The dial sleeve 56 can rotate relative to the driver 55 since the clutch teeth 53, 63 are disengaged. As a consequence, the dial sleeve 56 can rotate relative to the outer housing 54 and the inner housing 58.

Figure 5:
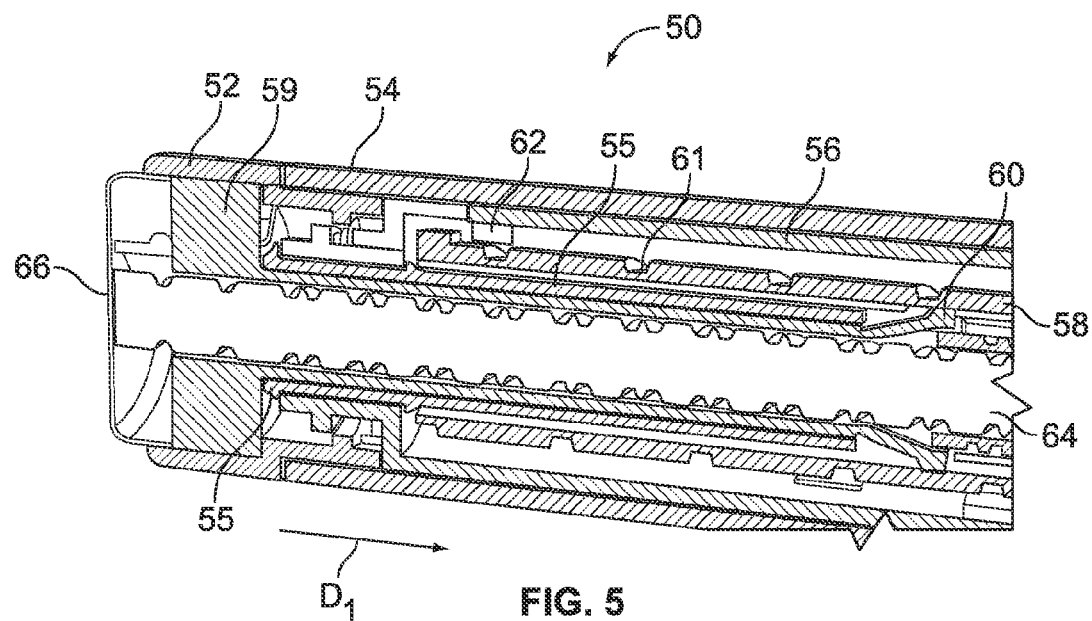
FIG. 5 illustrates a sectional view of the first arrangement in a dispensing state.
Figure 6:
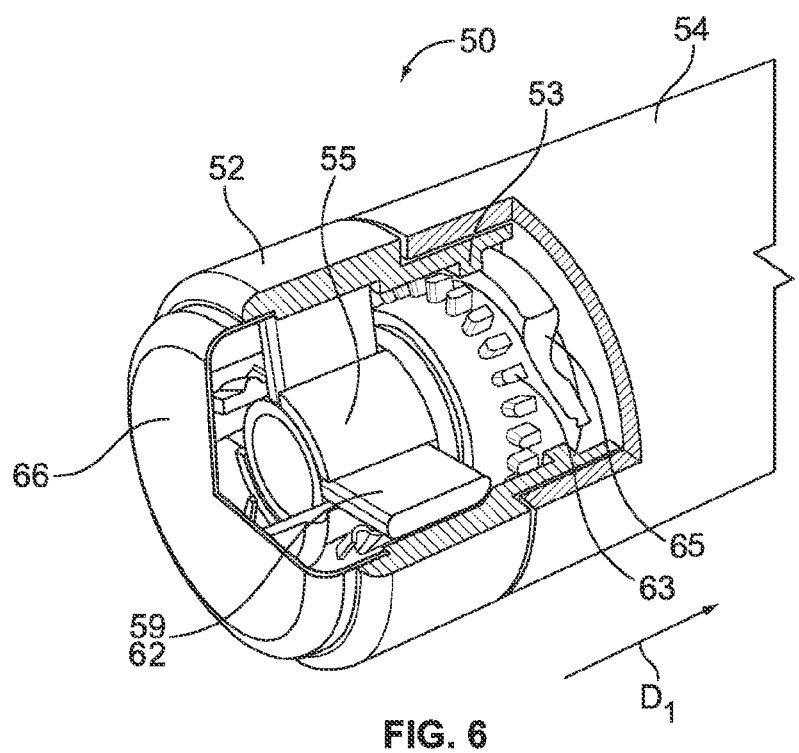
FIG. 6 is a partial perspective view of the dose setting mechanism illustrated in FIG. 5.

FIG. 5 illustrates the dose setting mechanism 50 illustrated in FIG. 3 in a dose dispensing state (i.e., during the injection of a previously dialled dose). FIG. 6 is a partial perspective view of the dose setting mechanism illustrated in FIG. 5. Referring now to both FIGS. 5 and 6, when the previously set dose is being dispensed, the user applies an axial load to the dose button 66. The dose button 66 is axially coupled to the clutch sleeve 59 and this coupling prevents relative axial movement. Therefore, the clutch sleeve 59 moves axially towards the cartridge end or the distal end of the dose setting mechanism 50 (direction D1). This movement disengages the clutch sleeve 59 from the dial sleeve 56. For example, as can be clearly seen from FIG. 6, axial movement of the button 66 moves the dose dial grip 52 in the distal direction D1. Specifically, movement of the dose dial grip 52 in this distal direction disengages the outwardly directed teeth 63 of the dial sleeve 56 from the inwardly radial extending teeth 53 of the dose dial grip 52. Disengaging these two components allows for the relative rotation of the dial sleeve 56 with respect to the outer housing 54, the clutch sleeve 59 and driver 55.

As described above, the clutch sleeve 59 is now prevented from rotating relative to the inner housing 58 since the clicker 60 is locked in splined engagement with the inner housing 58. However, in this scenario, the clutch 59 remains engaged with the driver 55.

Further, in the dispensing condition the clicker finger 65 operates together with second teeth provided on the inner surface of the dose dial grip 52 at its farthest distal end beside the first teeth 53. As the clicker finger 65 is coupled with the dial sleeve 56 which rotates during dispensing movement it produces a light clicker sound by sliding along the inward projecting second teeth of the dose dial grip 52.

Figure 7:
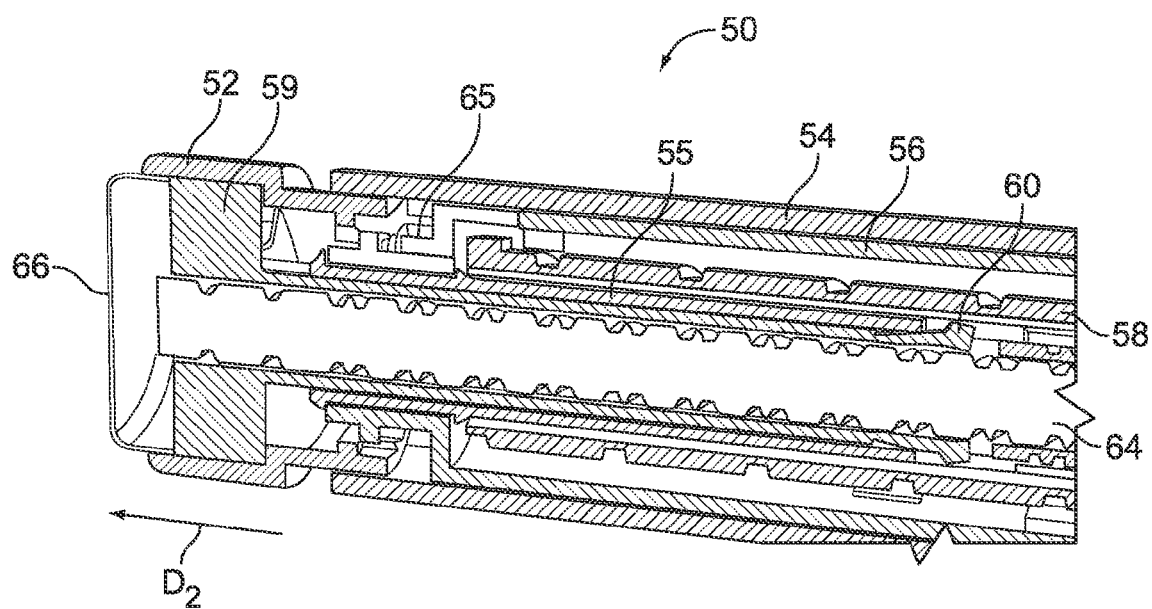
FIG. 7 illustrates a sectional view of the first arrangement in an initial device resetting condition.
Figure 8:
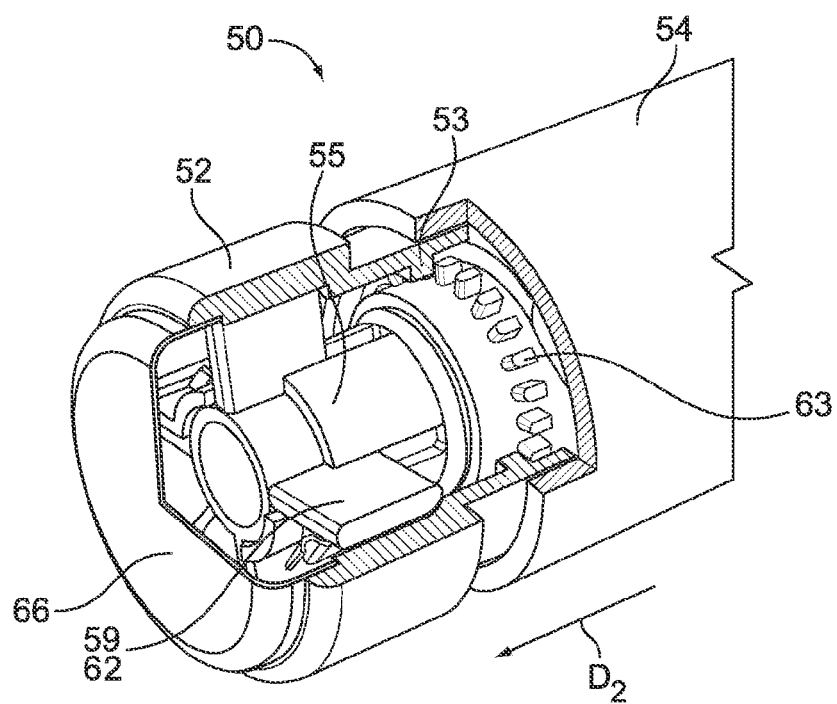
FIG. 8 is a partial perspective view of the dose setting mechanism illustrated in FIG. 7.

FIG. 7 illustrates the dose setting mechanism 50 shown in FIGS. 3 to 6 in a reset condition. FIG. 8 provides a close up illustration of the driver 55 rotationally decoupled from the dial sleeve 56 as illustrated in FIG. 7. Referring now to both FIGS. 7 and 8, in this reset condition, a user pulls the dose dial grip 52 in a proximal direction D2. That is, the user pulls the dose dial grip 52 away from the dose setting mechanism 50. This axial movement of the dose dial grip 52 allows the driver 55 and the dial sleeve 56 to become decoupled in rotation. This allows the driver 55 to rotate independently of the dial sleeve 56. The driver 55 and the inner housing 58 also become decoupled in rotation. In one preferred arrangement, the finger element 60 of the clutch sleeve 59 is retracted from the spline provided in the inner housing 58 into an opening of the driver 55 and slightly bent inward. Additionally the driver 55 can rotate relative to the dial sleeve 56 and the dose dial grip 52 since the clutch teeth 53, 63 are disengaged.

As shown in FIGS. 7 and 8, a user is required to pull the dose button 66 in the proximal direction D2 to place the dose setting mechanism 50 into a reset condition. Since the clutch sleeve 59 and driver 55 are free to rotate independently of the dial sleeve 56, the dose setting mechanism 50 may be reset by retracting the spindle 64 back into the dose setting mechanism 50, wherein the spindle 64 rotates. This can be accomplished by the user pushing the spindle 64 in the proximal direction D2. This re-sets the dose setting mechanism 50.

In one preferred arrangement, a detent mechanism is provided to retain the clutch sleeve 59, dial grip 52 and driver 55 in this reset condition illustrated in FIGS. 7 and 8. This detent mechanism preferably retains the clutch sleeve 59, dial grip 52 and driver 55 in this reset condition until a user presses the dose button 66 back in a distal direction, D1 (see, e.g., FIG. 5).

In this preferred first arrangement illustrated in FIGS. 3-8, a user is required to pull out the dose button 66 with the dose dial grip 52 to place the device into a reset condition. Once in the reset condition, the driver may be manipulated or rotated back to an initial start condition and then the spindle can be retracted back into the dose setting mechanism.

Figure 9:
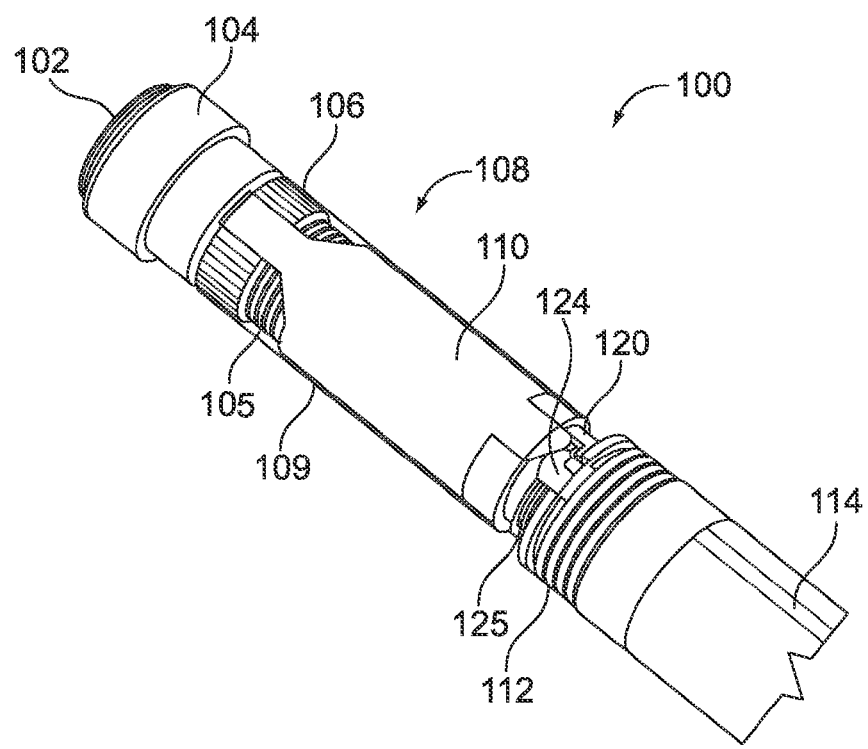
FIG. 9 illustrates a second arrangement of a drug delivery device according to a further aspect of the present invention in a partial perspective view.

FIG. 9 illustrates a second arrangement of a drug delivery device 100 according to another aspect of the present invention. The reset function of the drug delivery device 100 is different than that of the dose setting mechanism illustrated in FIGS. 3-8. For example, whereas the resetting function of the dose setting mechanism 50 is a manual operation, the resetting function of the drug delivery device 100 is semi-automatic.

The mechanical structure of the dose setting mechanism 108 is similar to the operation of the dose setting mechanism 50 illustrated in FIGS. 3-8. For example, the dose setting operation illustrated in FIGS. 3-4 the dose administration operation illustrated in FIGS. 5-6 and the decoupling of the mechanical elements illustrated in FIGS. 7-8 apply equally as well to how the dose setting mechanism 108 sets and then administers a dose.

One difference between the dose setting mechanism 108 of FIGS. 9-13 and the dose setting mechanism 50 illustrated in FIGS. 3-8 is that mechanism 108 includes an additional array of components that releasably interlocks the dose setting mechanism 108 with the cartridge holder 114. In one preferred arrangement, a clutch of the resettable dose setting mechanism 108 (similar to the clutch 59 of dose setting mechanism 50) is placed in a reset mode automatically. Preferably, this occurs automatically when the cartridge holder 114 is removed from the dose setting mechanism 108. Consequently, in this alternative arrangement, no additional steps on behalf of the user (or a patient caregiver) is required to place the dose setting mechanism 108 in its reset condition or a reset state. For example, in this alternative arrangement, the user is not required to manually pull back the dose dial sleeve so as to enable spindle retraction.

As illustrated, this drug delivery device 100 comprises a dose setting mechanism 108 releasably connected to a cartridge holder 114. This dose setting mechanism 108 is similar in operation to the dose setting mechanism 50 illustrated in FIG. 3. This dose setting mechanism 108 comprises a dose button 102 and a dose dial grip 104 at a proximal end of the dose setting mechanism 108. This mechanism further includes an interlock collar 120 (interlock latch) and a transfer sleeve 110. A dose dial sleeve 109 surrounds the transfer sleeve 110. The cartridge holder 114 comprises a removable cartridge (not illustrated in FIGS. 9-13), a spring 112, and a release sleeve 124 (cartridge holder retainer).

Figure 10:
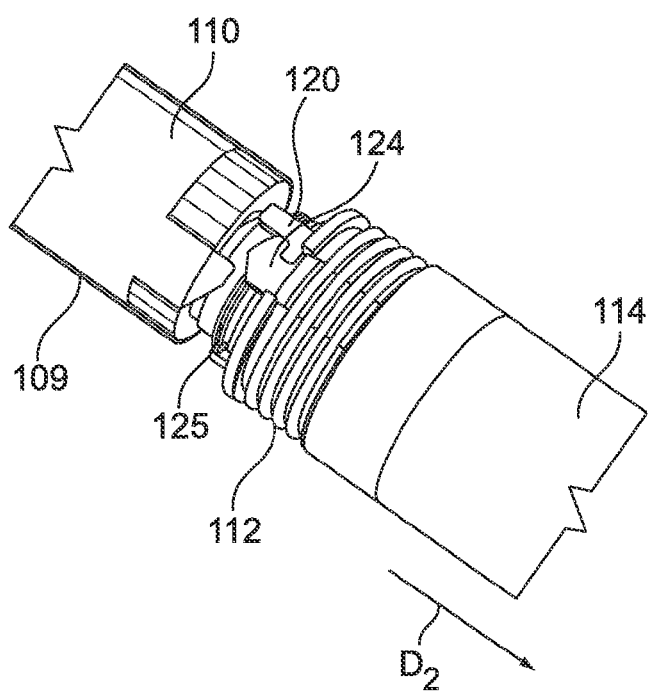
FIG. 10 illustrates the second arrangement in a partially dialled out position in a partial perspective view.

FIG. 10 illustrates the dose dial sleeve of FIG. 9 in a partially dialled out position. In FIG. 9 the dose dial sleeve is in zero dose position. In FIG. 10, the dial sleeve has been rotated a certain amount so as to select a dose. In this position, it can be seen that the interlock collar 120 is engaged with the release sleeve 124 driven by a rotational spring 125. This engagement prevents any movement of the release sleeve 124 in the forward or proximal direction D4. Therefore, this engagement also prevents a user from removing the cartridge holder 114 from the dose setting mechanism 108.

Figure 11:
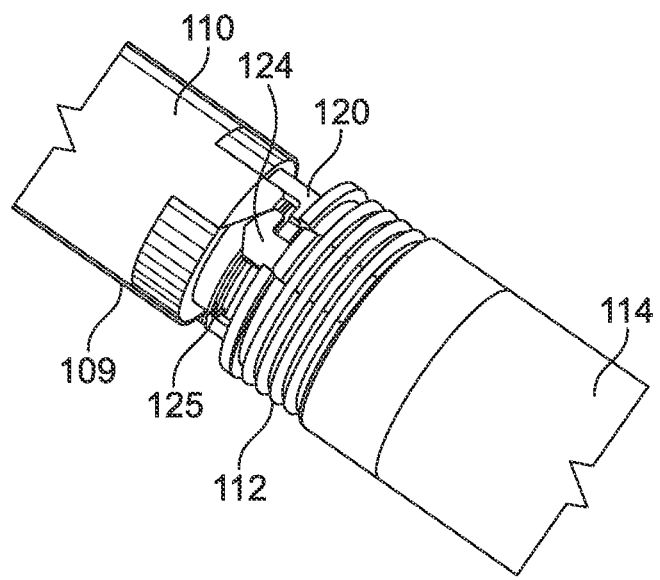
FIG. 11 illustrates the second arrangement in a fully dialled in position in a partial perspective view.

FIG. 11 illustrates the dose dial sleeve of FIG. 10 again in a fully dialled in position. As illustrated, the interlock collar 120 is disengaged from the release sleeve 124. This allows for forward movement of the release sleeve 124. Therefore, this disengagement also allows a user to remove the cartridge holder 114 from the dose setting mechanism 108. It is necessary to have the dial sleeve in a known (defined) position (for example the zero dose position) to enable the transfer sleeve 110 accurately.

Figure 12:
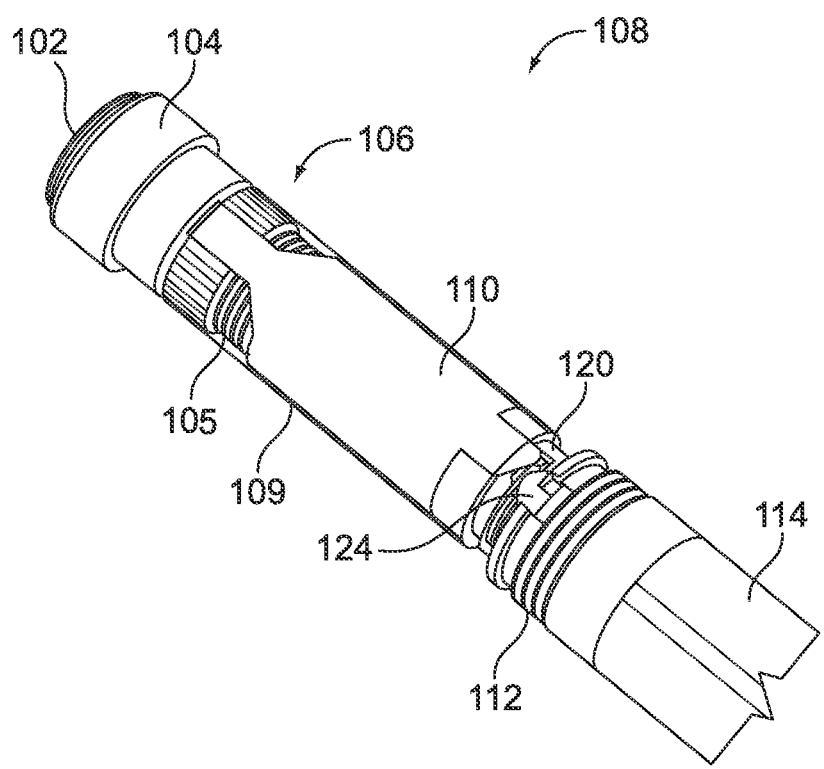
FIG. 12 illustrates the second arrangement in a position where the cartridge holder is partially disengaged from the dose setting mechanism in a partial perspective view.

FIG. 12 illustrates the interlock collar 120 disengaged from the release sleeve 124. This allows for forward movement (in proximal direction, D4) of the release sleeve 124 and hence removal of the cartridge holder 114.

Figure 13:
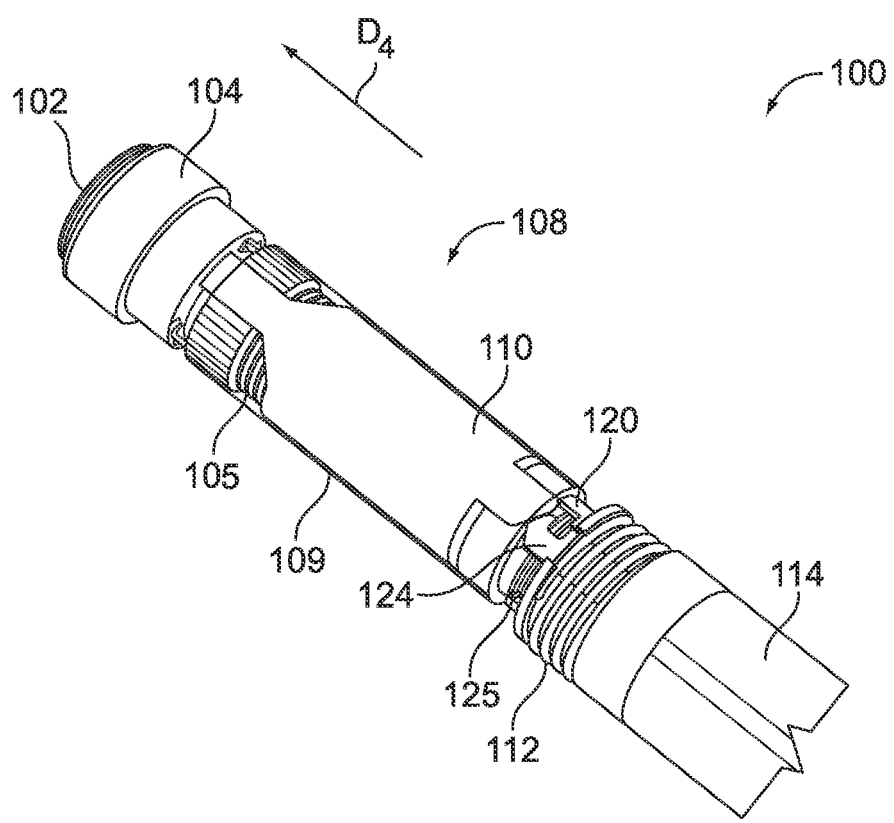
FIG. 13 illustrates the second arrangement in a position where the cartridge holder is disengaged from the dose setting mechanism.

FIG. 13 illustrates the cartridge holder 114 of FIG. 12 being disengaged from the dose setting mechanism 108 for example by a rotational movement of approximately 90°. This also allows the release spring 112 to push the release sleeve 124 and hence move the transfer sleeve 110 in a proximal direction D4 against a spring 105. As this transfer sleeve 110 moves in the proximal direction, it pushes the dose button 102 and the dose dial grip 104 in proximal direction D4 and places the clutch in the reset state.

When the cartridge holder 114 is removed from the dose setting mechanism 108, the release sleeve 124 is driven in the rearward or proximal direction. Preferably, this release sleeve 124 is spring loaded via a spring 112. The travel of the spring loaded release sleeve 124 causes the transfer sleeve 110 and dose button 102 of the dose setting mechanism 108 to also move in proximal direction D4.

Because the dose button 102 is operatively coupled to the driver, axial movement of the dose button 102 places both the clutch and the driver in a reset state. Consequently, as the cartridge holder 114 is removed and the dose setting mechanism 108 is automatically placed into a reset condition so that the spindle can be retracted back into the dose setting mechanism 108. The dose setting mechanism 108 may then be reset by turning the dial grip 104 that is engaged with the driver so that the driver may be rotated back to an initial starting position. Once the driver is returned to this initial position, a new cartridge containing medicament (i.e., such as a fast or slow acting insulin) may be placed in the cartridge holder 114 which may then be reconnected to the dose setting mechanism.

Exemplary embodiments of the present concepts have been described. Those skilled in the art will understand, however, that changes and modifications may be made to these embodiments without departing from the true scope and spirit of the present concepts, which is defined by the claims.

The invention claimed is:

1. A resettable dosing mechanism, said dosing mechanism comprising:
an inner housing preferably having at least one helical groove;
a dose dial sleeve rotationally engaged with the at least one helical groove of said housing;
a driver provided within said housing; and
a first clutch provided between said dial sleeve and said driver;
a second clutch between said inner housing and said driver;
wherein when a dose is set with said dose setting mechanism, said first clutch engages said dose dial sleeve and said driver to rotate together relative to said housing;
wherein when the set dose is injected, said first clutch disengages said dose dial sleeve from said driver while said second clutch couples said driver to said inner housing,
so that said dose dial sleeve rotates and said driver is prevented from rotating but moves axially against a spindle to expel said set dose; and
wherein when resetting said dosing mechanism, said first clutch decouples said driver from said dose dial sleeve and said second clutch decouples said driver from said housing, allowing said driver to be moved to a reset position.

2. The mechanism of claim 1 wherein said driver is moved in an axial direction in order to place said driver in said reset position.

3. The mechanism of claim 1 wherein said driver is moved in a proximal direction in order to rotate said driver in said reset condition.

4. The mechanism of claim 1 further comprising a cartridge holder coupled to said dose setting mechanism, wherein the cartridge holder comprises a cartridge containing a medicament.

5. The mechanism of claim 1 wherein said housing comprises said helical groove along an outer surface.

6. The mechanism of claim 1 wherein said driver is operatively coupled to a dose dial grip, wherein said dose dial grip is rotatable to set said dose of medication.

7. The mechanism of claim 1 wherein said dose dial sleeve comprises a scale arrangement, said scale arrangement indicative of said dose is set with said dosing mechanism.

8. The mechanism claim 1 further comprising a spindle operatively connected to the driver, where the spindle is configured to be retracted axially back in a proximal direction when the second clutch decouples the driver from the housing.

9. A resettable drug delivery device, said device comprising:
a cartridge holder comprising a releasable mechanical interlock;
a resettable dosing mechanism comprising,
an inner housing preferably having at least one helical groove;
a dose dial sleeve rotationally engaged with the at least one helical groove of said housing;
a driver provided within said housing
a spindle operatively connected to the driver;
a first clutch provided between said dial sleeve and said driver;
a second clutch between said inner housing and said driver; and
a dose dial grip or a dose button operativey engaged with the first clutch and configured so that a user is not required to manually pull the dose dial grip or the dose button in a proximal direction to reset the resettable dosing mechanism;
wherein when a dose is set with said resettable dosing mechanism, said first clutch engages said dose dial sleeve and said driver to rotate together relative to said housing;

wherein when the set dose is injected, said first clutch disengages said dose dial sleeve from said driver while said second clutch couples said driver to said inner housing, so that said dose dial sleeve rotates and said driver is prevented from rotating but moves axially against the spindle to expel said set dose; and where the dose setting mechanism is releasably coupled to said mechanical interlock, wherein during resetting of the dosing mechanism the spindle is retracted back into the resettable dosing mechanism, wherein a user is not required to manually pull back the dose dial grip or dose button in a proximal direction in order to enable spindle retraction back into the resettable dosing mechanism said dosing mechanism further comprising a transfer sleeve operatively engaged with said dose button or said dose dial grip, and a rotatable dose setting sleeve surrounding said transfer sleeve, such that when said dose setting sleeve is rotated to reach a predetermined position, said dose setting sleeve releases said mechanical interlock and places said resettable dose setting mechanism in a reset condition.

10. The device of claim 9 wherein said releasable mechanical interlock further comprises a release sleeve, said release sleeve releasably coupling an interlock collar of said dose setting mechanism.

11. The device of claim 9 further comprising a release spring operatively coupled to said release sleeve of said cartridge holder, such that when said cartridge holder disengages from said resettable dose setting mechanism, said release spring moves said release sleeve in a proximal direction.

12. The device of claim 9 wherein when said release sleeve is pushed in said proximal direction, said release sleeve acts on said transfer sleeve of said resettable dose setting mechanism and moves said transfer sleeve in a proximal direction.

* * * * *